(12) United States Patent
Pessin

(10) Patent No.: US 7,938,808 B2
(45) Date of Patent: May 10, 2011

(54) INJECTION DEVICE COMPRISING A SYRINGE

(75) Inventor: Olivier Pessin, Grezieu la Varenne (FR)

(73) Assignee: Sedat, Irigny (FR)

( * ) Notice: Subject to any disclaimer, the term of this patent is extended or adjusted under 35 U.S.C. 154(b) by 1042 days.

(21) Appl. No.: 11/574,176

(22) PCT Filed: Jul. 25, 2005

(86) PCT No.: PCT/FR2005/001926
§ 371 (c)(1),
(2), (4) Date: May 2, 2007

(87) PCT Pub. No.: WO2006/027445
PCT Pub. Date: Mar. 16, 2006

(65) Prior Publication Data
US 2007/0265576 A1    Nov. 15, 2007

(30) Foreign Application Priority Data
Aug. 27, 2004  (FR) ...................... 04 09162

(51) Int. Cl.
*A61M 5/32* (2006.01)
(52) U.S. Cl. ........................ 604/192; 604/110
(58) Field of Classification Search .................. 604/110, 604/111, 192, 198, 197, 187, 232, 263, 218; 606/108
See application file for complete search history.

(56) References Cited

U.S. PATENT DOCUMENTS

| 4,927,416 | A * | 5/1990 | Tomkiel ..................... 604/198 |
| 5,163,918 | A * | 11/1992 | Righi et al. .................. 604/198 |
| 5,803,918 | A | 9/1998 | Vetter et al. |
| 6,296,625 | B1 | 10/2001 | Vetter et al. |
| 6,416,323 | B1 | 7/2002 | Grenfell et al. |
| 2002/0045864 | A1 | 4/2002 | Perez et al. |
| 2004/0144668 | A1 | 7/2004 | Marshall et al. |

FOREIGN PATENT DOCUMENTS

| EP | 904 792 | 3/1999 |
| FR | 2 837 107 | 9/2003 |

* cited by examiner

*Primary Examiner* — Christopher D Koharski
(74) *Attorney, Agent, or Firm* — Sughrue Mion, PLLC

(57) ABSTRACT

The invention relates to an injection device, comprising an injection syringe (1) with a tubular syringe body, provided at a porximal end with a fixing collar (16), projecting radially outwards, an injection piston, arranged to slide within the body, a needle protection device (2), comprising a protector support (20) and a sliding needle protector (22). The device comprises a stop pin (25) for the piston stop (8), said pin (25) is mounted on the protector support (20) and defines, in the extension of the syringe body, a piston circulation passage of which the minimum section is larger than the section of the running part (10) of the piston and less than the section of a shoulder (15) of the piston.

8 Claims, 7 Drawing Sheets

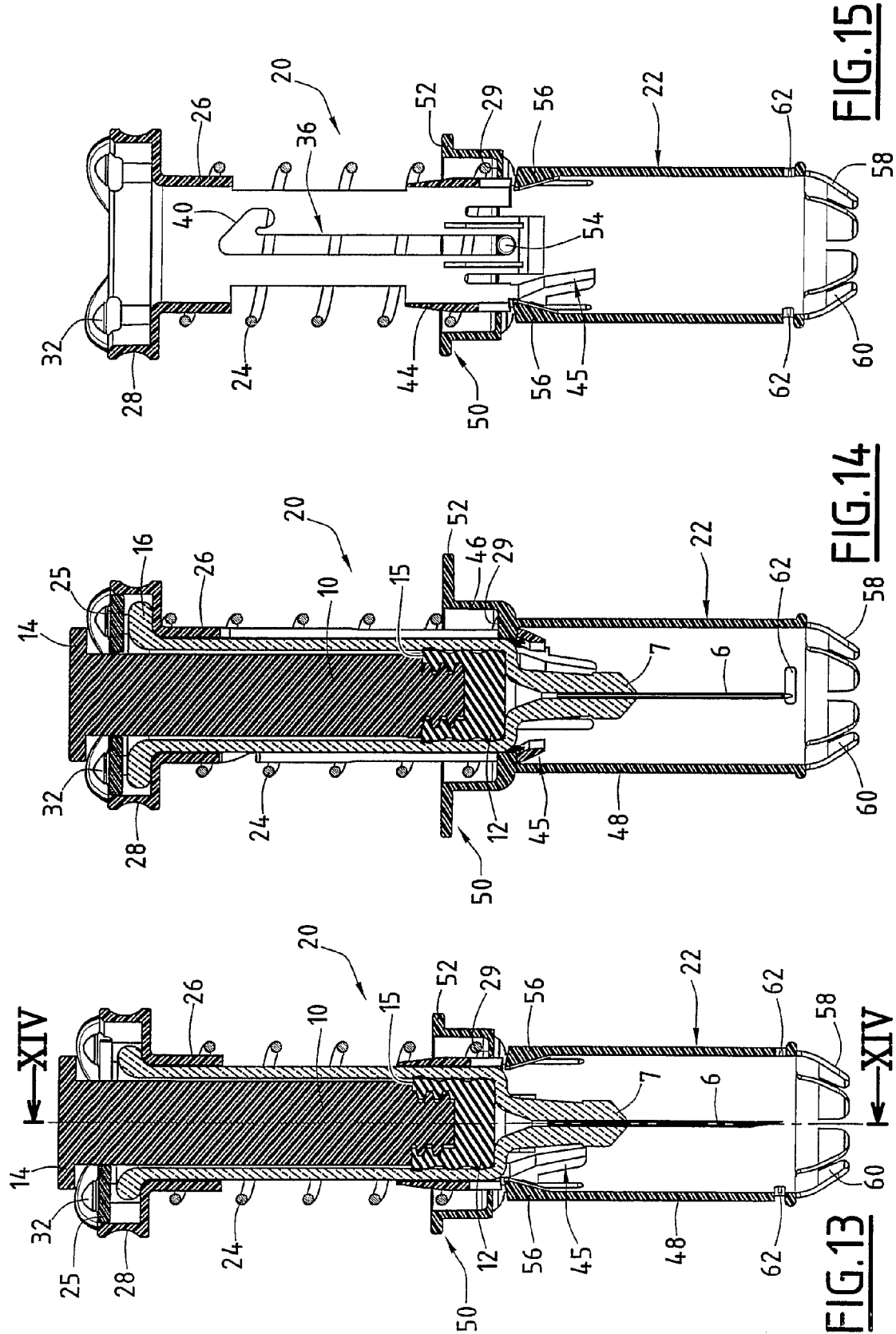

INJECTION DEVICE COMPRISING A SYRINGE

The present invention relates to a needle protection device comprising:
- an injection syringe comprising:
  - a tubular syringe body equipped at a proximal end with a fixing collar projecting radially outward; and
  - an injection plunger mounted to slide within the body by being introduced into the body from the proximal end of the body
- a needle protection device comprising:
  - a protector support delimiting a conduit for receiving the syringe body, which protector support comprises means for axially fixing the body relative to the protector support,
  - a needle protector mounted so as to be displaceable relative to the protector support between a retracted position and an extended position.

The invention concerns, in particular, the field of pre-filled disposable injection syringes intended, in particular, for intramuscular or subcutaneous injections.

These devices are intended to minimise the risk of the user being accidentally jabbed after the injection, since once the content of the syringe has been injected, the needle of the syringe is withdrawn from the patient and the protector is automatically brought into the extended position beyond the injecting end of the needle.

A protection device of this type is described, in particular, in document FR 2 837 107.

In this device, the needle protection device is attached to the syringe body. For this purpose, the protection device comprises a protector support delimiting a cylindrical passage with which the syringe body is engaged. At its proximal end, the protector support comprises resilient interlocking means for fixing the syringe body from a peripheral flange arranged at the distal end thereof In order to perform an intramuscular injection, a practitioner, having injected the needle, will often carry out a "vein test" to check that it is a muscle, as intended, rather than a vein that he has injected. To carry out this test, the practitioner pulls the plunger of the syringe backward. If too great a pull is exerted, the plunger can become completely disengaged from the syringe body, thus rendering the injection device entirely unusable, since the liquid contained in the syringe is then in contact with the air.

The device described in document FR 2 837 107 does not solve this problem of detachment of the plunger from the syringe body in the event of an excessive pull being exerted on the plunger.

Such a risk also exists during take-up of lyophilisate, i.e. on intake into the syringe body from the needle of an extemporaneous mixture prepared immediately prior to injection.

The object of the invention is to propose an injection device which is equipped with an attached needle protection device and reduces the risk of the plunger being drawn out of the syringe body by the exertion of a pull on the plunger.

The invention accordingly relates to an injection device of the aforementioned type, characterised in that the plunger comprises a distal end engaged in the syringe body and extended toward the proximal end by a common portion of the plunger, a shoulder turned toward the proximal end being defined between the distal end and the common portion of the plunger, and in that it comprises a stop clip for stopping the plunger, which clip is carried by the protector support and defines, in the extension of the syringe body, a passage for the travel of the plunger, the minimum section of which is greater than the section of the common portion of the plunger and is smaller than the section of the plunger shoulder.

According to further characteristics of this device, taken in isolation or in any technically feasible combination:
- the clip delimits a notch which opens radially and the base of which delimits said travel passage for the plunger;
- the protector support comprises means for resiliently interlocking the clip for the axial fixing thereof,
- the resilient interlocking means comprise click-lock projections carried by the protector support, the distance between said click-lock projections being greater than the section of the syringe body to allow free engagement of the syringe body in the protector support;
- orifices are formed along the click-lock projections to impart resilience thereto;
- the protector support comprises a stop for axially supporting the syringe body toward the proximal end and the clip is axially connected to the protector support toward the proximal end and forms a stop for stopping the collar toward the proximal end so that the collar is axially confined between the support stop and the clip;
- the clip has a circular outer contour.

The invention will be better understood on reading the following description, given merely by way of example and with reference to the drawings, in which:

FIG. 13 to 15 show the injection device in the extended position, FIG. 13 being a view similar to that of FIG. 10, FIG. 14 being a cross-section along the plane XIV-XIV indicated in FIG. 13 and FIG. 15 being a view identical to that of FIG. 13, the syringe not being shown.

FIG. 1 is a perspective view of an injection device formed by a syringe 1 and a protection unit 2. The terms "proximal" and "rear" are used hereinafter as synonyms, as are the terms "distal" and "front".

Figure 1:
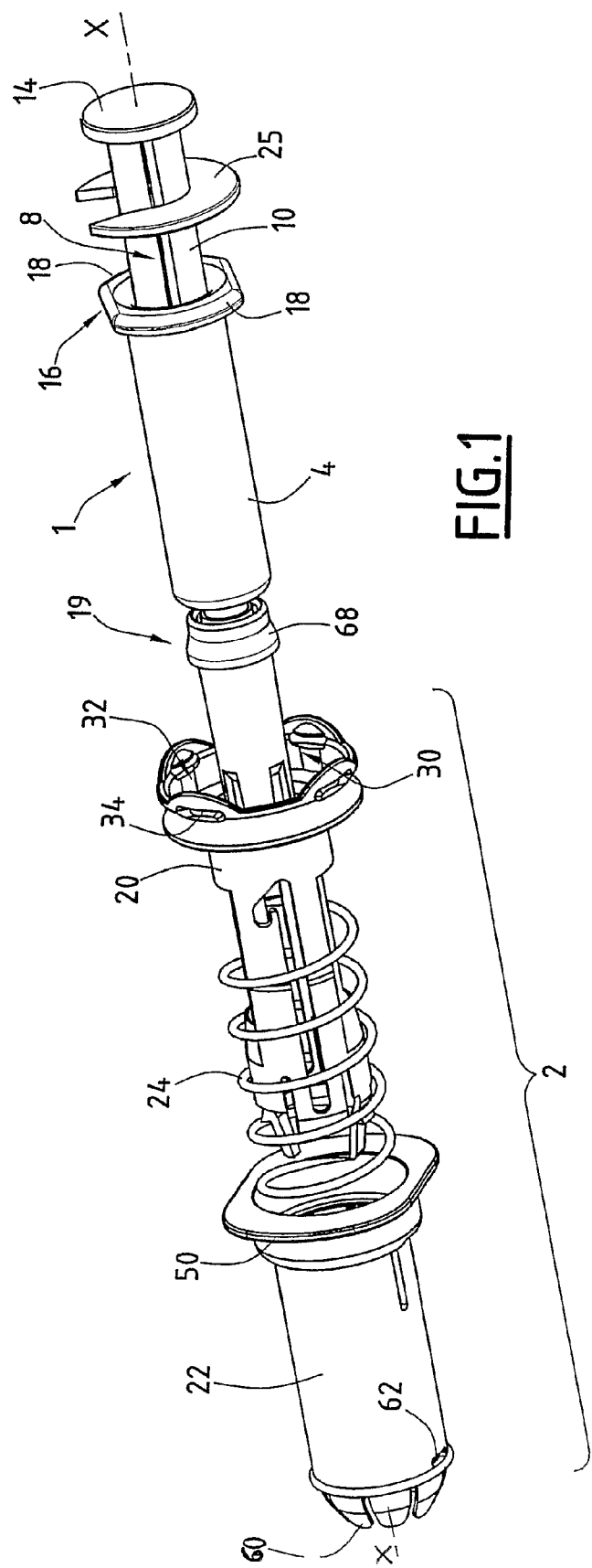
FIG. 1 is an exploded perspective view of an injection device according to the invention prior to assembly.

The syringe 1 is a glass syringe of standard shape and intended for a single use. It contains a liquid to be injected, intramuscularly or subcutaneously, into a patient. It therefore comprises a body 4 and a needle 6 as may be seen, in particular, in FIG. 6. This needle is joined to the distal end of the body 4 by a ferrule 7.

The syringe further comprises a plunger 8 engaged in the body 4. This plunger conventionally comprises a rod 10 provided at its distal end with a plug 12, as may be seen in FIG. 6, and with a support head 14 on which the thumb of the practitioner's hand is intended to rest.

Figure 6:
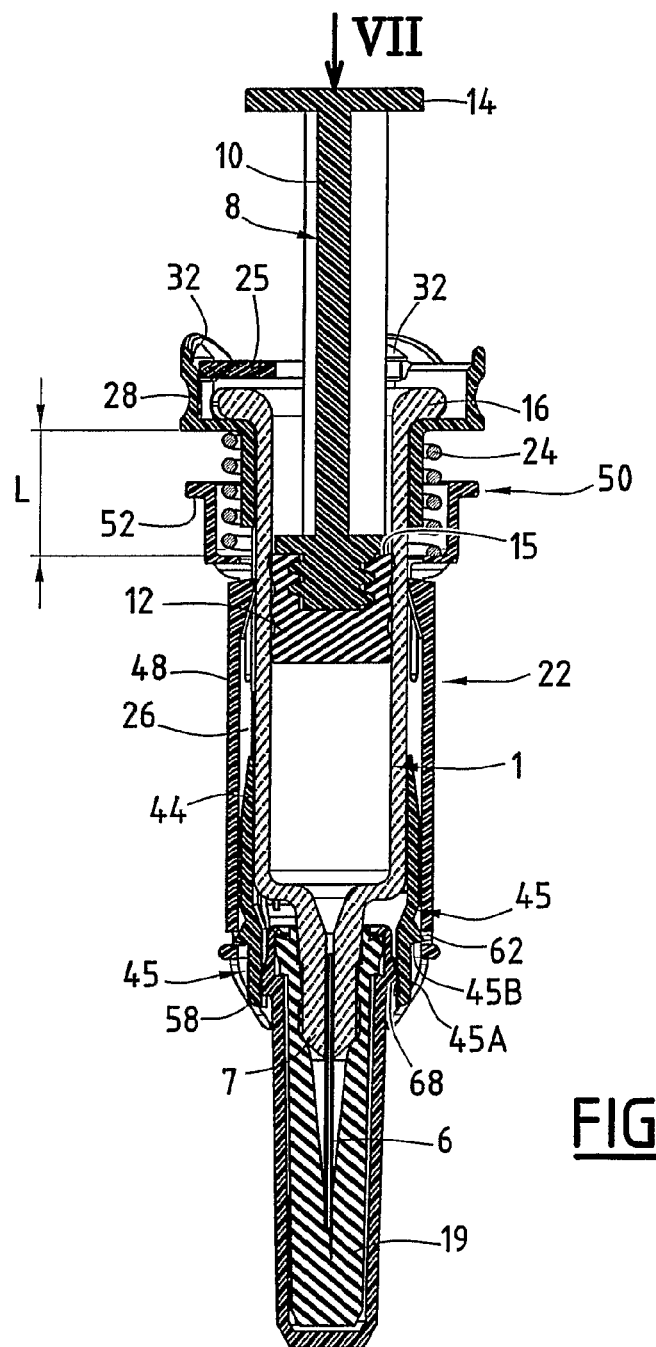
FIG. 6 is a view, along the same sectional plane as in FIG. 5, of the injection device according to the invention prior to use.

The rod 10 has, in its common portion, a section smaller than that of the plug 12, thus forming a peripheral shoulder 15, as may be seen in FIG. 6, on the plug 12 around the rod 10.

The syringe body 4 comprises, in its proximal portion, a collar 16 circumferentially delimiting two diametrically opposed lugs 18 normally intended, in particular in the absence of the unit 2, to form support surfaces for the practitioner's index and middle fingers when handling the syringe and injecting the liquid located therein.

Initially, the needle 6 is protected by a movable cap 19 fixed to the body of the syringe by being engaged on the ferrule 7.

The protection unit 2, having a general axis X-X, basically comprises, as shown in FIG. 1:
- a generally tubular support 20;
- a protective sleeve 22 arranged coaxially with the support 20 and having a diameter greater than that of the support,
- a spring 14; and
- a clip 25 for stopping the plunger and for attaching the syringe to the protective unit.

Figure 2:
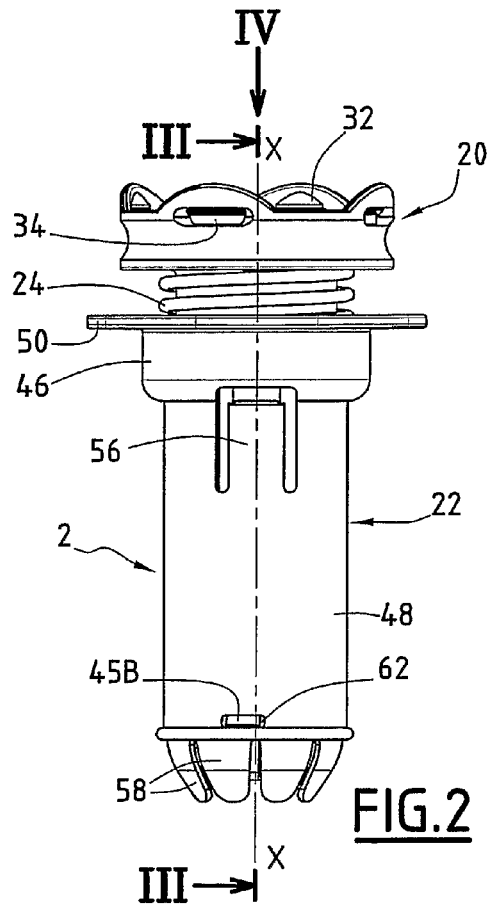
FIG. 2 is an elevation of the protection device pertaining to the injection device of FIG. 1, in the retracted position.

These elements will each be described in detail hereinafter with reference to FIG. 2 to 4.

The support 20 comprises a substantially cylindrical main portion 26 having an internal diameter substantially equal to the external diameter of the syringe body 4. This portion 26 has two diametrically opposed longitudinal recesses 26A. The portion 26 is extended, at is proximal end, by a secondary portion 28 having greater internal and external diameters than those of the main portion 26, forming a radial shoulder 29. The portion 28 has an internal diameter greater than the maximum diameter of the syringe collar 16.

The proximal portion 28 is provided with means 30 for fixing the clip 25 so that said clip surrounds the syringe collar 16 between the shoulder 29 and the clip 25, as shown in FIG. 6.

Figure 4:
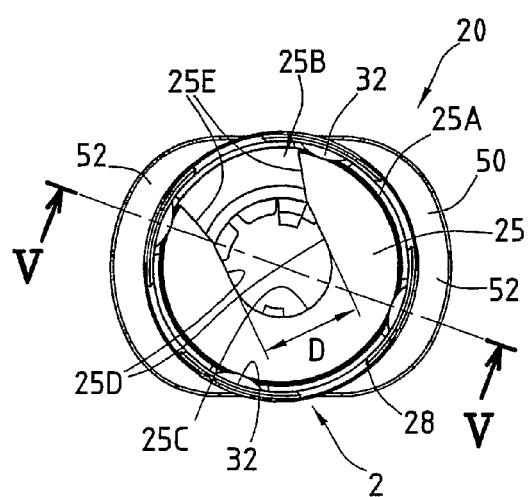
FIG. 4 is a plan view in the direction of arrow IV indicated in FIG. 2.

The clip 25, as may be seen in FIG. 4, is planar and is in the shape of a hollowed disc so as to form a U. It is delimited at its periphery by a circular contour 25A, the diameter of which is very slightly smaller than the internal diameter of the secondary portion 28. It has a notch 25B engaging in the disc forming the clip beyond the centre thereof This notch 25B opens radially at the periphery of the disc forming the clip. It has a semi-circular base 25C and two parallel lips 25D extending the base 25C. These lips 25D are extended, up to the periphery 25A of the disc, by divergent faces 25E, so the notch 25B flares in the vicinity of its opening end.

The diameter of the base 25C and the distance separating the lips 25D, both designated by D, are chosen to be greater than the diameter of the common portion of the plunger rod 10 and smaller than the diameter of the plug 12 extending the rod 10. This diameter D is thus smaller than the internal section of the syringe body 4.

The fixing means 30 comprise diametrically opposed deformable hooks 32 which are carried by the portion 28 of the protector support. These hooks may be seen, in particular, in FIGS. 1 and 5. The distance separating the diametrically opposed hooks is smaller than the external diameter of the clip 25. Orifices 34 are formed in the portion 28 along the hooks 32 to impart resilience to said hooks.

Each of these hooks forms a substantially truncated cone-shaped ramp 32A flaring toward the free end of the portion 28. These ramps 32A are intended to allow the hooks to be pushed resiliently outward under the effect of the clip 25 when the support 20 is fixed to the syringe 1. The hooks 32 are set apart from the shoulder 29 by a distance substantially equal to the cumulative thicknesses of the lugs 18 and the clip 25. The hooks 32 thus form a clip-on engagement means for the clip 25 for fixing the syringe collar 16.

Two cruciform through-grooves 36 are formed, one facing the other, in the main portion 26. Each groove consists of a first rectilinear portion 38, extending substantially along the axis X-X of the support 20 over a length greater than that of the needle 6, and of a second rectilinear portion 40, extending in an inclined manner relative to the same axis X-X. The inclined portion 40 opens at the proximal end of the first rectilinear portion 38, forming a V, the point of which is directed away from the proximal side of the unit 2.

Figure 5:
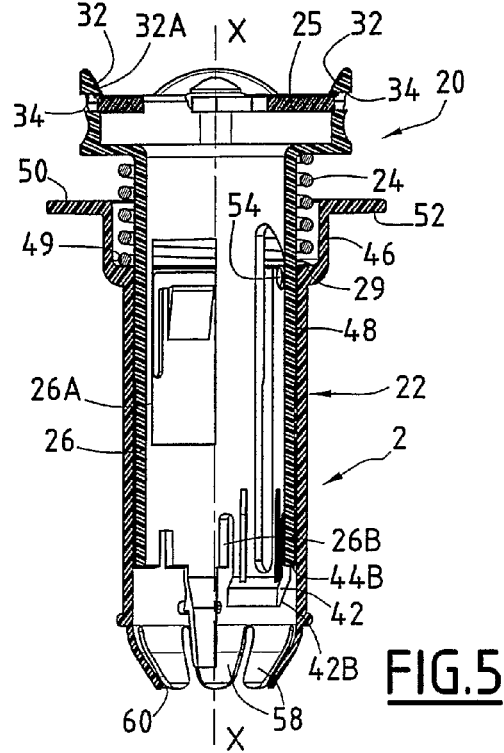
FIG. 5 is a cross-section along the plane V-V indicated in FIG. 4.

The main portion 26 comprises, at its distal end, a pair of diametrically opposed resilient tongues 42, each located in the extension of the grooves 36 (FIG. 5). These tongues 42 have a substantially cylindrical inner face 42A and a substantially truncated cone-shaped outer face 42B diverging toward the rear.

The main portion 26 comprises a pair of diametrically opposed outer ramps 44 located between the resilient tongues along the circumference of the distal end of this portion. They have a substantially truncated cone-shaped inclined outer surface 44A, diverging toward the front, and a substantially planar distal surface 44B. The outer surfaces 44A are thus turned toward the recesses 26A.

The longitudinal recesses 26A are formed in the main portion 26 (FIG. 3) at the proximal end of these ramps 44.

Furthermore, either side of the tongues 42, axial slots 26B are provided from the distal end of the support so that, prior to insertion of the body 4 of the syringe 1 within the support 20, these tongues 42 are radially deformable, especially inwardly.

At its distal or front end, the main portion 26 has, between the resilient tongues 42, two further tongues 45 for axially joining the protector 22 and the protector support 20 in the presence of the protective cap 19 placed over the syringe body.

Figure 3:
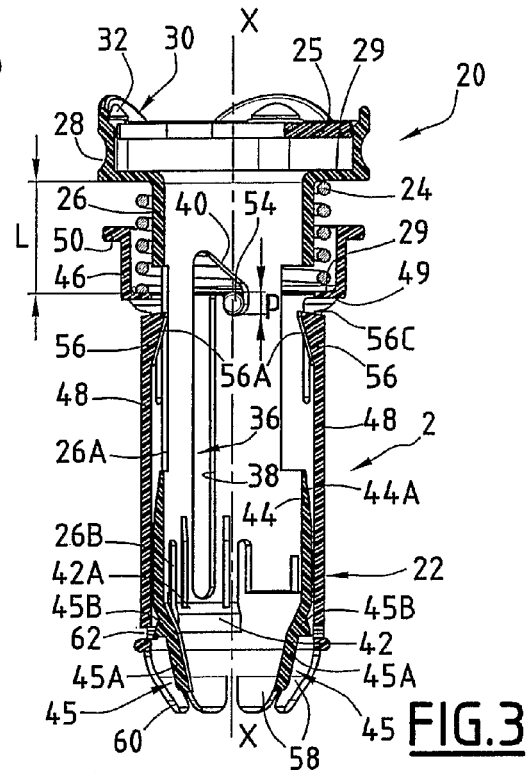
FIG. 3 is a cross-section along the plane III-III indicated in FIG. 2.

More specifically, and as shown in FIG. 3, these tongues each comprise a leg 45A extending the main portion 26 and integral therewith. Each leg 45A carries, on its outside, a projection 45B capable of engaging with a complementary orifice formed in the protector.

The projections 45B are provided over half of the length of the legs 45A, extending from the region at which the legs are connected to the main portion 26. The legs 45A thus extend beyond the projections 45B.

As shown in FIG. 3, the tongues are, in the rest state, inclined toward the axis X-X of the support, i.e. they converge toward one another in the direction of their free end and they extend in the extension of the inner passage delimited by the protector support.

These tongues 45 are outwardly resiliently deformable so that, in the rest position, the projections are contained entirely within the extension of the general bulk of the main portion 26 whereas, in the deformed position, the projections 45B extend radially outward beyond the extension of the general bulk of the main portion 26.

The distance separating the free ends of the two tongues 45, when they are in their rest position, is smaller than the minimum external diameter of the ring for fixing the protective syringe cap 19.

The length of the protective sleeve 22 is substantially equal to that of the syringe body 4. The sleeve consists of two cylindrical portions 46 and 48, the diameter of the proximal portion 46 being slightly greater than that of the main portion 48. These two portions connect to form a radial shoulder 49.

The sleeve 22 integrally comprises, in its proximal portion, an outer flange 50 in the form of two diametrically opposed lugs 52 (FIGS. 4 and 5).

Also in its proximal portion, but within the protective sleeve 22, two diametrically opposed studs 54 are integral with the sleeve (FIG. 5). These two studs are received and guided in the two grooves 36 in the support respectively. The support and the sleeve can thus be moved in translation relative to each other along the common axis thereof and in limited rotation about the same axis when the studs are in the inclined portions 40. The inclined portions 40 then form pockets for fixing the studs 54, these pockets having a fixing depth denoted by p in FIG. 3. This depth is measured along the axis of the protector.

The support 20 and the sleeve 22 are movable between a retracted position of the sleeve, in which most of the sleeve covers most of the support and the studs 54 are located at the distal end of each of the inclined groove portions 40 as illustrated in FIG. 2 to 8, and an extended position of the sleeve, in which said sleeve projects axially from the support and the studs are located at the distal end of the rectilinear groove portion 38 as illustrated in FIG. 13 to 15.

When the syringe 1 is fixed to the unit 2, these end positions correspond respectively to an injection configuration in which the needle 6 of the syringe 1 is released and intended to be inserted into a patient and to a protective configuration in which this needle is surrounded by the protective sleeve 22.

The proximal portion of the sleeve 22 further comprises, on its inside, a pair of diametrically opposed deformable longitudinal hooks 56. These hooks are delimited in the sleeve 22 by lateral slots. Their distal end is connected to the sleeve. At its free proximal end, each hook has an inner protrusion.

In the absence of the syringe, and as shown in FIG. 3, the outer surfaces of the hooks 56 extend in the extension of the sleeve. The inner protrusions of these hooks, on the other hand, project inside the cylindrical passage delimited by the sleeve 22. Each protrusion has a substantially truncated cone-shaped front face 56A extending toward the front of the axis of the sleeve 22. These front faces 56A are thus turned toward the front end of the protector.

Each front face 56A is adapted to cooperate with an inclined surface 44A formed by the ramps 44 of the support.

At its free end, each hook 56 has an inclined transverse front 56C forming a stop.

In the retracted position of the sleeve, the hooks 56 extend inside recesses 26A formed in the support 20. In the extended position of the sleeve, as shown in FIG. 13, the end faces 56C of the hooks 56 axially abut the tongues 42, the hooks and tongues thus forming a rigid locking unit in the extended position.

The sleeve 22 is further provided, at the distal end thereof, with a crown of deformable tongues 58, the distal edges of which form a substantially circular opening 60, the diameter of which is smaller than the internal diameter of the main portion 26 of the support 20.

Finally, at it distal end, the main portion 48 of the protective sleeve comprises two oblong through-orifices 62 capable of receiving the projections 45B carried by the second pair of tongues 45 when these tongues are deformed under the effect of the ring of the needle protection cap 19 engaged on a syringe contained in the device.

In the absence of a cap, i.e. when the tongues 45 are in their rest position, the projections 45B are entirely outside the orifices 62, allowing free displacement of the protector relative to the support.

The spring 24 is a spiral spring arranged between the protective sleeve 22 and the protector support 20. More specifically, the spring is accommodated between the shoulder 29 of the support 20 and the shoulder 49 of the sleeve 22.

In the retracted position of the sleeve, the spring 24 is in a compressed state, thus having decompression energy associated with the rigidity of the spring and with the difference between the length of the spring in the rest state and the length thereof, denoted by L in FIG. 2 to 8, in the compressed state. In other words, the spring 24 has an additional compressive force threshold corresponding to the minimum force required further to compress the spring from its initial compressed state as shown in FIG. 2 to 8. The stiffness of the spring and/or the initial compression length L are chosen so that this force threshold is greater than the thrust required to displace the plunger 8 of the syringe 1 throughout the injection stroke thereof More specifically, the force of the spring in the locked state is greater than the sum of the injection force, i.e. the force for discharging the liquid out of the needle 6 of the syringe 1, and the stresses for the detachment and sliding of the pusher 12 within the syringe body 4.

The cap 19 is generally tubular in shape and is shown in FIGS. 1 and 6.

It is adapted to surround the needle 6 prior to use of the syringe 1. This cap is closed at one of its ends and its opposing end is formed by an annular ring 68, the external diameter of which is suitable both for being joined to the surface 42A of the tongues 42 and for being greater than the diameter of the opening 60 formed by the tongues 58 of the protective sleeve 22. The inner face of this ring 68 is intended to adhere to the glass ferrule 7 of the syringe body where the needle 6 is fixed, in particular for ensuring a degree of imperviousness to bacteria.

Furthermore, the external diameter of the ring 68 of the cap is greater than the distance separating the free ends of the tongues 45, in the rest state.

The injection device according to the invention operates as follows.

The protection device 2 is assembled in its retracted configuration, i.e. that of FIG. 2 to 8. For this purpose, the protective sleeve 22 is slipped around the support 20 from the distal end of the support, providing the spring 24 therebetween. More specifically, the sleeve 22 is axially displaced toward the rear relative to the support, while at the same time outwardly radially deforming the hooks 56 using a suitable tool, at least until they axially reach the front portion of the longitudinal recesses 26A.

Then, while still displacing the sleeve toward the rear, the studs 54 are applied against the outer surfaces 42B of the tongues 42, inwardly deforming said tongues until the pegs are received in the rectilinear portions 38. The protector 22 is then displaced toward the rear until the studs 54 are received in the inclined groove portions 40 by causing the support and the protector to pivot relative to each other. The protector is thus in the retracted position.

The glass syringe 1 is pre-filled with a liquid to be injected into a patient. This syringe is equipped with the cap 19 which surrounds the ferrule 9 of the syringe body 4.

Figure 7:
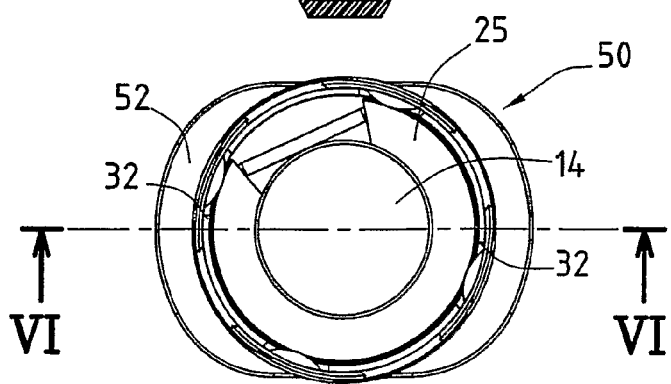
FIG. 7 is a plan view in the direction of arrow VII indicated in FIG. 6.

The syringe equipped with the cap 19 is inserted inside the unit 2 to form the injection device as shown in FIGS. 6 and 7. More specifically, the body 4 of the syringe is displaced substantially axially within the support 20.

The syringe body is displaced in the protector until the syringe collar 16 rests against the shoulder 29.

In this position, the clip 25 is then attached to the collar 16. For this purpose, if the plunger rod 10 is already mounted on the plug 12, the clip 25 is engaged around the plunger rod, the plunger rod being in the notch. The clip 25 is displaced along the length of the rod 10, then engaged with the main portion 28, thus radially outwardly deforming the hooks 32 so as resiliently to interlock the clip.

The lugs 18 of the syringe collar 16 are then fixed axially by the clip 25, itself fixed by the hooks 32.

If the syringe collar 16 is entirely clipped on inside the portion 28, it can no longer fulfil its conventional role of forming a support surface for the practitioner's index and middle fingers. This support function is performed by the flange 50 which is integral with the sleeve 22. If the length of the protective sleeve 22 is substantially equal to that of the syringe body 4 and/or the flange 50 is provided in the region of the proximal end of this sleeve, the practitioner can then handle the syringe by resting his thumb on the support head 14 of the plunger 8, and by resting his index and middle fingers on the faces of the lugs 52 directed toward the needle 6.

Moreover, if the syringe 1 is fixed to the protector support 20 as shown in FIGS. 6 and 7, the cap 19 projects outside the protective sleeve 22.

Furthermore, the widened external diameter of the ring 68 of the cap is engaged between the free ends of the tongues 45, thus radially outwardly deforming them. Under the effect of this deformation, the projections 45B are received in the orifices 62. In this position, the cooperation of the projections 45B, carried by the protector support, and the orifices 62 formed in the protector axially joins the protector and the support, thus preventing release of the spring, the stud 54 being unable to leave the end of the cross with which it is engaged.

When the practitioner is ready to inject the liquid contained in the syringe, he withdraws the cap 19 by pulling it axially forward.

To withdraw the cap, the practitioner can hold the syringe, fixing the protector from the support surfaces 50 with one hand, and pull on the cap 19 with the other hand. Even if there is a very high degree of resistance to the withdrawal of the cap, the positive axial connection provided by the projections 45B, which are engaged in the orifices 62, prevents the spring 24 from being able to be compressed and the studs 54 from being able to be released outside the fixing cross.

There is therefore no risk of the needle protector being accidentally released when the cap is withdrawn.

On the other hand, after withdrawal of the cap as shown in FIG. 7, the protector 22 can be displaced relative to the support 20, since the tongues 45 resume their rest position under the effect of the resilience thereof and the projections 45A are then released from the orifices 62.

After the detachment of the ring 68 from the ferrule 9, the ring 68 passes through the opening 60 by deforming the tongues 58. Once the cap 19 has been withdrawn, the tongues 58 resume their initial position.

The practitioner may then have cause to carry out an operation known as a "vein test". This consists in checking that the syringe has been injected correctly into a patient's muscle and not into an artery or a vein. For this purpose, the plunger 8 is pulled toward the proximal end. If blood is drawn into the syringe body, the practitioner will deduce that the needle has been injected into a vein or an artery and will then start again to position the needle.

Figure 9:
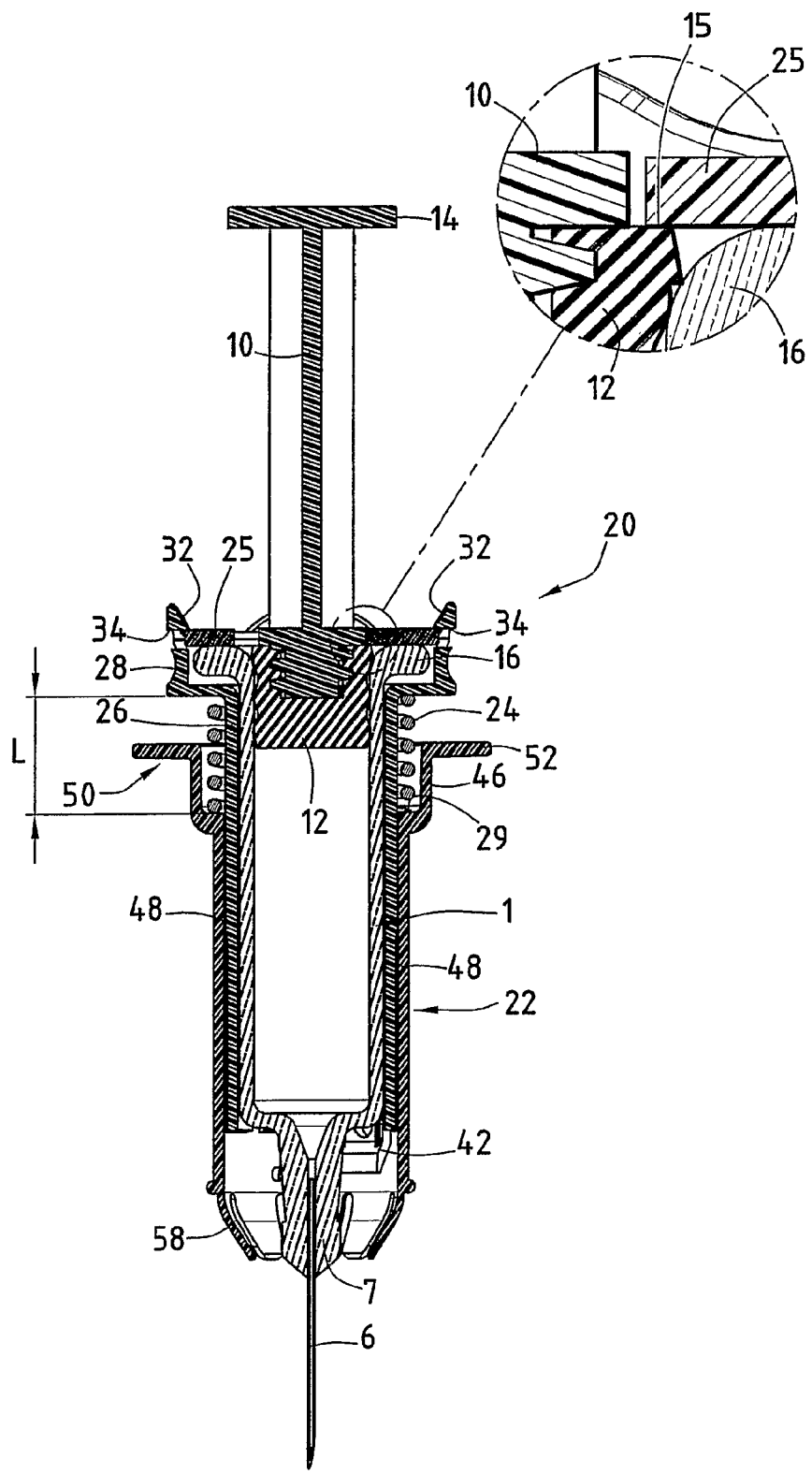
FIG. 9 is an identical view to that of FIG. 8, the plunger of the injection device being withdrawn into the end position.

In the event of an excessive pull being exerted by the practitioner onto the plunger rod, the plug 12 is halted in its displacement by abutting, via the shoulder 15, the clip 25 as illustrated in FIG. 9. The notch 25B defines a passage, the section of which is smaller than the section of the plug 12, thus preventing the plug from passing beyond the clip. The plunger rod 10, on the other hand, which has a smaller diameter, is able to slide freely through the notch 25B.

It will thus be understood that the clip 25 both fixes the syringe body 4 in the protector and forms a stop for stopping the plug 12 in the event of an excessive pull being exerted thereon. If the clip were not there, the plug could be extracted from the syringe body, thus rendering the injection device unusable.

The stopping of the plunger in the event of an excessive pull being exerted thereon is also useful during filling of the syringe through the needle, for example during take-up of lyophilisate.

Figure 8:
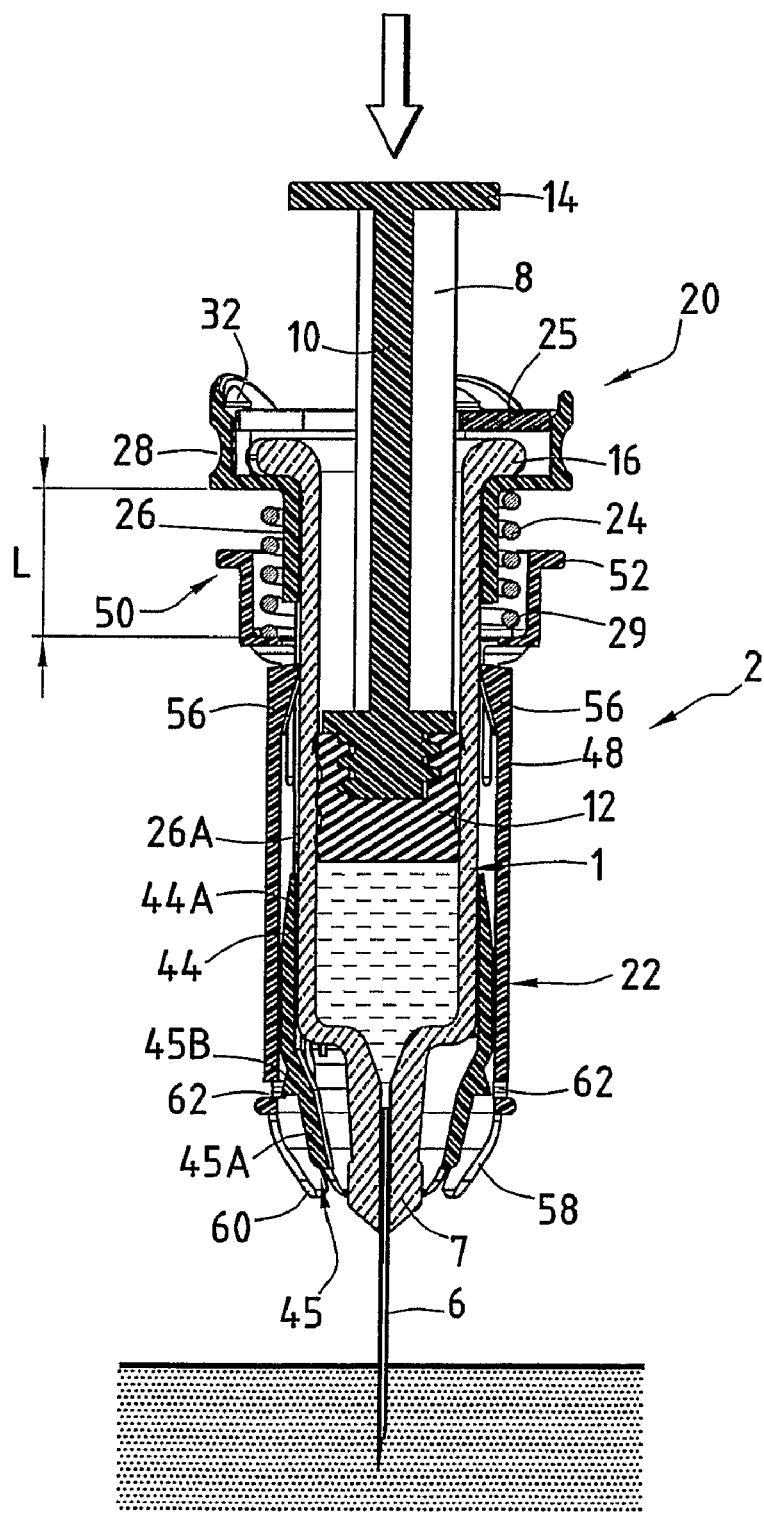
FIG. 8 is a view similar to that of FIG. 6, the injection device being ready for use.

In order to commence the injection process itself, the practitioner expels the liquid contained in the syringe by exerting a pushing force onto the support head 14 of the plunger, his index and middle fingers remaining in contact with the faces directed toward the needle of the lugs 52. During the injection there is no movement between the protector support 20 and the protective sleeve 22, the spring 24 remaining compressed at a length L as shown in FIG. 8.

The injection process is continued until the pusher 12 of the plunger 8 reaches the end of the injection stroke.

Figure 12:
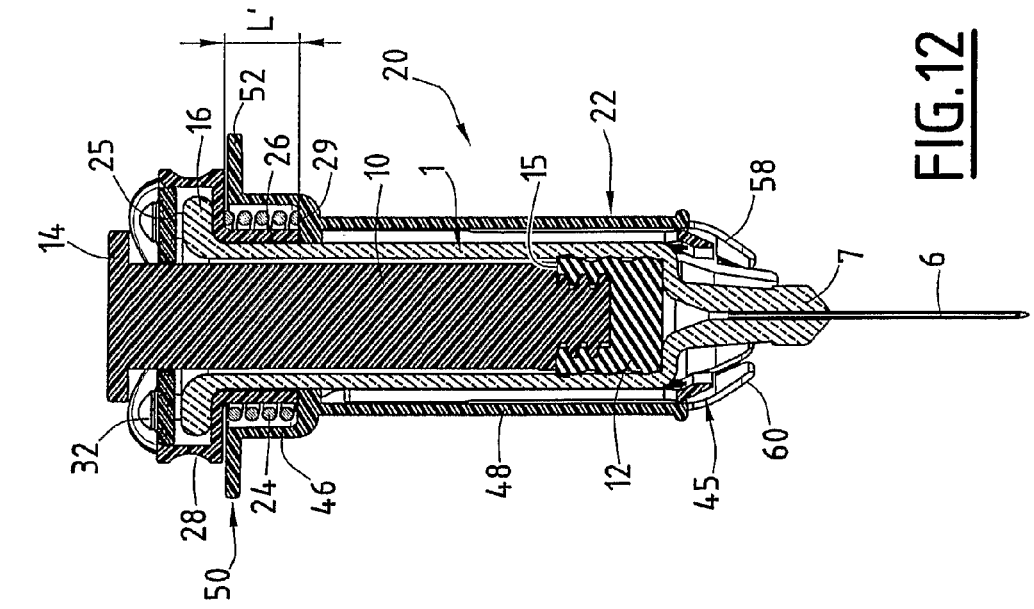
FIG. 12 is a cross-section along the plane XII-XII indicated in FIG. 10.
Figure 11:
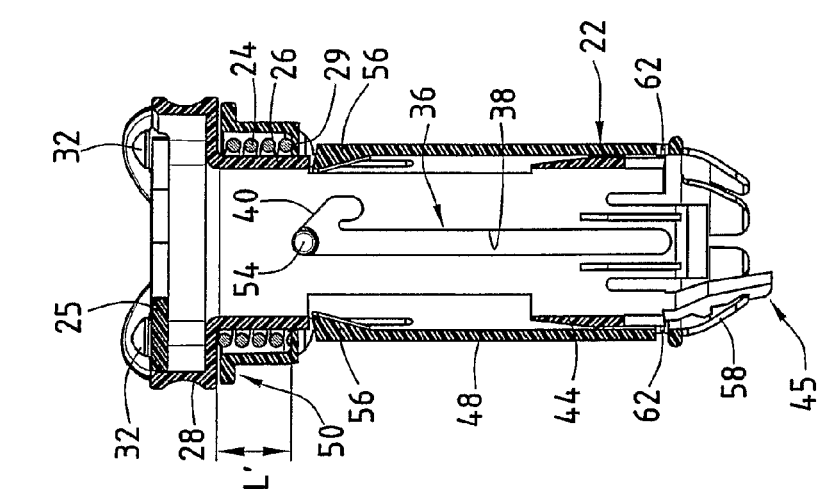
FIG. 11 is a view identical to that of FIG. 10, the syringe of the injection device not being shown.
Figure 10:
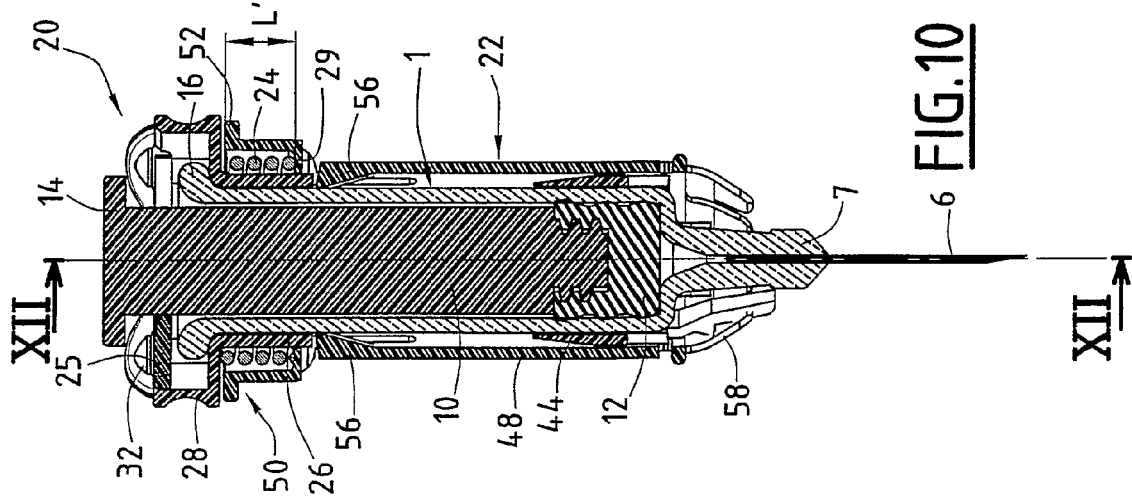
FIG. 10 is a view, along the same sectional plane as in FIG. 3, of the injection device at the end of use.

The practitioner then withdraws the needle from the patient. To release the protective unit 2, the practitioner subjects the plunger rod 8 to additional pressure. This pressure must be greater than the predetermined force produced by the spring 24 in the locked state, so that the spring is more compressed and passes from its length L to a shorter length L' as shown in FIG. 10 to 12. In order to do this, assuming a fixed syringe, the protective sleeve 22 is displaced axially toward the proximal end of the support 20. The practitioner performs this movement by exerting a corresponding pressure, using his index and middle fingers, on the lugs 52 of the flange 50 of the sleeve 22. This pressure, in combination with the translatory movement, causes the protective sleeve 22 to rotate about the syringe support 20, the studs 54 being guided by the inclined groove portions 40. This rotational movement continues until the studs reach the proximal end of this groove portion 40, i.e. the proximal end of the longitudinal groove portion 38, as may be seen in FIG. 11. The device 2 is then in the position for unlocking the spring 24.

The practitioner then releases the pressure previously exerted on the flange 50, allowing the spring 24 to relax into a rest state. The studs 54 are displaced in translation within the longitudinal groove portion 38, up to the distal end thereof, as shown in FIG. 13 to 15. The practitioner is able to control the translational movement of the protective sleeve 22 relative to the support 20 by gradually releasing his grip on the flange 50. Once the studs 54 have reached the distal end of the groove 36 (FIG. 15), the protector is in its extended position.

Furthermore, when the protective sleeve 22 is undergoing translational movement relative to the support 20, the hooks 56 lend support to the longitudinal recesses 26A until they slide along the distal ends 44 of the support by cooperation of their complementary surfaces 56A and 44A.

In the extended position of the protector, the hooks 56 are held by cooperation of the surfaces 56C and 44B, thus preventing the protector sleeve 22 from being brought into its initial position. Similarly, the sleeve 22 cannot easily be torn from the support 20, since the studs 54 abut the distal base of the longitudinal groove portion 38 (FIG. 15), the tongues 42 forming this base being radially held between the body of the syringe 1 and the protective sleeve 22.

The injection device according to the invention is thus easy to use while allowing the practitioner to control the movement of the protective sleeve covering the needle. The number of parts of which the protective unit 2 shown consists is reduced to three.

The device according to the invention can be adapted to various types of syringe, with regard to both shape and volume. This device therefore has the advantage of not challenging the general shape of the syringes used and accordingly does not necessitate any modification of the industrial processes for filling these syringes.

Differing variations of the device according to the invention are conceivable:

- unlike the embodiment described hereinbefore, the studs 54 and/or the flange 50 of the protective sleeve 22 can be added to the sleeve 22 rather than being formed in one piece therewith;
- in contrast to the described device, the studs 54 can be provided over the outer surface of the protector support 20 and the guide groove 36 formed in the protective sleeve 22; and/or
- the support 20 can be formed in one piece with the syringe body 4.

The invention claimed is:

1. An injection device comprising:
   an injection syringe comprising:
      a tubular syringe body equipped at a proximal end with a fixing collar projecting radially outward; and
      an injection plunger mounted to slide within the body by being introduced into the body from the proximal end of the body, the plunger comprising a distal end, provided with a plug, engaged in the syringe body and extended toward the proximal end by a common portion of the plunger, the plug comprising a shoulder turned toward the proximal end and defined between the distal end and the common portion of the plunger, and
   a needle protection device comprising:
      a protector support delimiting a conduit for receiving the syringe body, which protector support comprises means for axially fixing the body relative to the protector support,
      a needle protector mounted so as to be displaceable relative to the protector support between a retracted position and an extended position,
      wherein the device comprises a stop clip for stopping the plunger, which clip is planar and is in the shape of a hollowed disc so as to form a U, said clip being carried by the protector support and defining, in the extension of the syringe body, a travel passage for the plunger, the minimum section of which is greater than the section of the common portion of the plunger and is smaller than the section of the plunger shoulder.

2. Injection device according to claim 1, characterised in that the clip (25) delimits a notch (25B) which opens radially and the base (25C) of which delimits said travel passage for the plunger (8).

3. Injection device according to claim 2, characterised in that the distance separating the lips (25D) delimiting the notch is chosen to be greater than the diameter of the common portion of the plunger (10) and smaller than the internal section of the syringe body (4).

4. Injection device according to claim 1, characterised in that the protector support (20) comprises means (32) for resiliently interlocking the clip (25) for the axial fixing thereof.

5. Injection device according to claim 4, characterised in that the resilient interlocking means comprise click-lock projections (32) carried by the protector support (20), the distance between said click-lock projections (32) being greater than the section of the syringe body to allow free engagement of the syringe body (4) with the protector support (20).

6. Injection device according to claim 5, characterised in that orifices (34) are formed along the click-lock projections (32) to impart resilience thereto.

7. Injection device according to claim 1, characterised in that the protector support (20) comprises a stop (29) for axially supporting the syringe body (4) toward the proximal end and in that the clip (25) is axially connected to the protector support (20) toward the proximal end and forms a stop for stopping the collar (16) toward the proximal end so that the collar (16) is axially confined between the support stop (29) and the clip (25).

8. Injection device according to claim 1, characterised in that the clip (25) has a circular outer contour.

\* \* \* \* \*